United States Patent [19]

Koga

[11] Patent Number: 4,962,517

[45] Date of Patent: Oct. 9, 1990

[54] AUTOMATIC X-RAY CORRECTION DEVICE

[75] Inventor: Toshiyuki Koga, Tokyo, Japan

[73] Assignee: Seiko Instruments Inc., Japan

[21] Appl. No.: 780,966

[22] Filed: Sep. 25, 1985

Related U.S. Application Data

[63] Continuation of Ser. No. 500,251, Jun. 2, 1983, abandoned, and Ser. No. 533,543, Sep. 17, 1983, abandoned.

[30] Foreign Application Priority Data

Jun. 3, 1982 [JP] Japan .................................. 57-82823
Sep. 24, 1982 [JP] Japan ................................ 57-166269

[51] Int. Cl.⁵ .......................................... G01N 23/223
[52] U.S. Cl. ....................................... 378/48; 378/160
[58] Field of Search ...................... 378/48, 44, 45, 160

[56] References Cited

U.S. PATENT DOCUMENTS 4,362,935 12/1982 Clark, III ............................... 378/48

Primary Examiner—Craig E. Church
Attorney, Agent, or Firm—Bruce L. Adams; Van C. Wilks

[57] ABSTRACT

An X-ray device comprising an X-ray tube (1); a shutter (9) which is movable between an open position (not shown) in which X-rays from the X-ray tube (1) may be directed onto material (8) to be tested and a closed position (shown in FIG. 1) in which the said X-rays are prevented from being so directed; an X-ray detector (4) for detecting fluorescent X-rays emitted by said material (8) when the shutter (9) is open; means (2) movable with the shutter (9) for receiving X-rays from the X-ray tube (1) and for directing fluorescent X-rays onto the X-ray detector (4) when the shutter (9) is closed; and correction means (11–14) connected to said X-ray detector (4) for automatically correcting a change in the X-rays produced by the X-ray tube (1).

15 Claims, 3 Drawing Sheets

AUTOMATIC X-RAY CORRECTION DEVICE

This is a continuation-in-part of Ser. No. 500,251 filed June 2, 1983 and of Ser. No. 533,543 filed Sept. 19, 1983 both abandoned.

BACKGROUND OF THE INVENTION

This invention related to an X-ray device and, although the invention is not so restricted, it more particularly relates to and X-ray device having an X-ray tube which is arranged to be corrected for any change in the intensity and/or wave height of the X-rays produced by the tube.

The conventional type, X-ray device as shown in FIG. 4, comprises an X-ray tube 1 and an X-ray detector 4 which has openings 5a, 5b for the transmission of X-rays thereto. The X-ray detector 4 is arranged to receive X-rays from the X-ray tube 1 by way of a guide passage 20 which communicates with the opening 5a, and the X-ray detector 4 is also arranged to receive fluorescent X-rays which are reflected from sample material 8, by way of the opening 5b. The X-ray tube 1 is provided with a shutter 21 which is movable between an open position, in which X-rays from the X-ray tube 1 may be directed onto the sample material 8 so that fluorescent X-rays may be reflected from the sample 8 and onto the X-ray detector 4, and a closed position in which the sample material 8 is prevented from receiving X-rays from the X-ray tube 1. The X-ray detector 4 is connected to a wave height discriminator 11, a scaler timer 12, and an automatic correction means 13 for correcting the X-rays produced by the X-ray tube 1 when the X-ray intensity and/or wave height change.

In the known construction shown in FIG. 4, corrected X-rays (i.e. X-rays whose intensity and/or wave height have been adjusted) are directed from the X-ray tube 1 onto the X-ray detector 4 while the shutter 21 is opened and the sample material 8 is receiving X-rays from the X-ray tube 1. However, there is an overlap between the spectrum of the X-rays from the X-ray tube 1 and the spectrum of the X-rays from the sample material 8 and this makes it difficult to effect an accurate measurement of certain properties of the sample material 8, e.g. the thickness of a layer thereon.

Generally, an X-ray correction is executed by measuring fluorescent X-rays irradiated from a sample after irradiating an X-rays on a correction sample. A certain measuring time for the fluorescent X-rays for exactly correcting the X-ray device is necessary.

Therefore, in an X-ray device in which X-ray correction is executed during the period that being a sample is not being measured, i.e., a shutter is kept in while the closed condition, measurement of a sample can not be executed until the fluorescent X-ray measurement for correction is finished.

SUMMARY OF THE INVENTION

This invention aims to eliminate the above noted difficulty and insufficiency, an object of the present invention being to provide a means for guiding a correction fluorescent X-rays to an X-ray detector only during a non-operation period, i.e., when the shutter is closed.

And the present invention aims to eliminate the above noted difficulty and insufficiency, particularly, in the case of starting a measurement for a sample at a time when a fluorescent X-ray measurement from a correction sample is not finished, measurement data obtained from a prior correction sample is memorized and used to correct the X-ray device.

PREFERRED EMBODIMENT OF THE INVENTION

Figure 1:
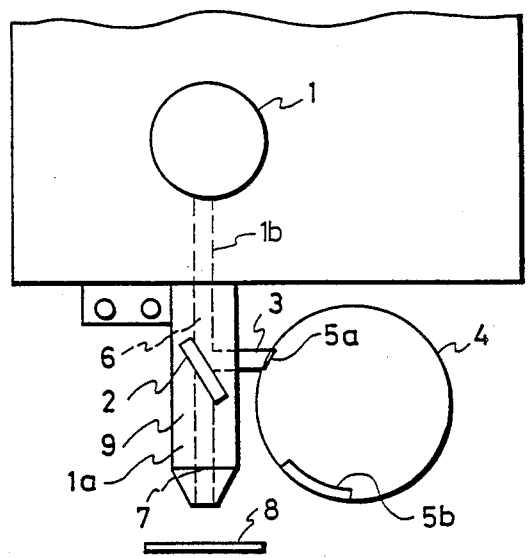
FIG. 1 is a diagrammatic view of an X-ray device according to the present invention.
Figure 2:
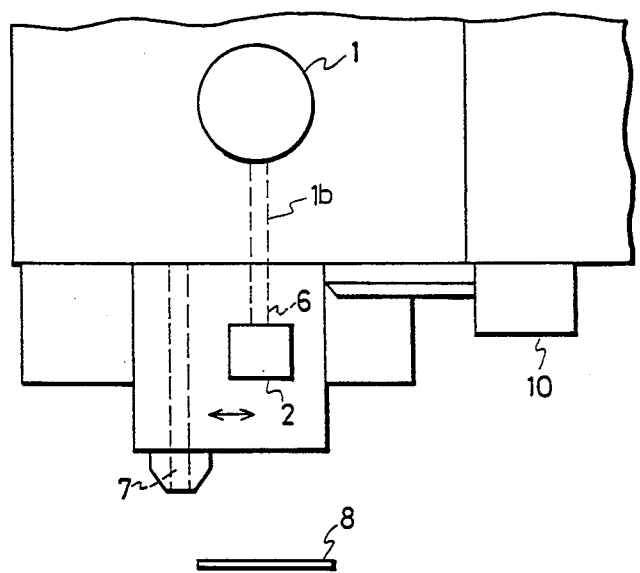
FIG. 2 is a diagrammatic view of the X-ray device shown in FIG. 1, the view of FIG. 2 being at right angles to that of FIG. 1.

As shown in FIGS. 1 and 2, an X-ray device according to the present invention comprises an X-ray tube 1 and a shutter 9. The shutter 9 is movable between an open position (not shown), in which X-rays from the X-ray tube 1 may be directed along an X-ray path through a passage 1b onto a sample material 8 to be tested, and a closed position (shown in FIG. 1) in which the X-rays from the X-ray tube 1 are prevented from being directed onto the sample. The shutter 9 has a collimator 1a for collimating the X-rays from the X-ray tube 1. The collimator 1a has a first guide passage 6 therein which is arranged to receive X-rays from the passage 1b of the X-ray tube 1 and to collimate the X-rays because of its large diameter, and a second guide passage 3 which communicates with the guide passage 6, and a third guide passage 7 which can communicate with the passage 1b. Mounted on the shutter 9 and carried thereby so as to be movable therewith is a correction standard plate 2 which may be a thin gold plate or may be similar in composition and construction to that of the sample material 8. Thus if the sample material 8 is intended to be provided with a layer of a specific material having a specific thickness, the correction standard plate 2 is similarly provided with such a layer.

When the correction standard plate 2 is in the position shown in FIG. 1 and is thus in the position in which the shutter 9 is closed, X-rays which are directed through the passage 1a and first guide passage 6 onto the correction standard plate 2 will produce fluorescent X-rays which will be directed through the second guide passage 3 and through an opening 5a onto an X-ray detector 4 which may comprise a proportional counter or other suitable detecting device.

The third guide passage 7 is arranged to direct X-rays from the passage 1b onto the sample material 8 only when the shutter 9 is open. That is to say, the passage 1b and the third passage 7 communicate with each other only when the shutter 9 is open, these passages being out of communication with each other when the shutter 9 is closed as shown in FIG. 2. Fluorescent X-rays produced by the sample material 8 are directed onto the X-ray detector 4 by way of an opening 5b therein. The X-ray detector 4, which is thus responsive to the fluorescent X-rays produced by the sample material 8, produces signals related to these fluorescent X-rays, and means (not shown) are provided which are responsive to these signals for indicating the value of a property of the sample material 8 (e.g. the thickness of a surface layer thereon) or for exercising a control (e.g. the control of the thickness of said layer) in dependence upon said value.

Figure 3:
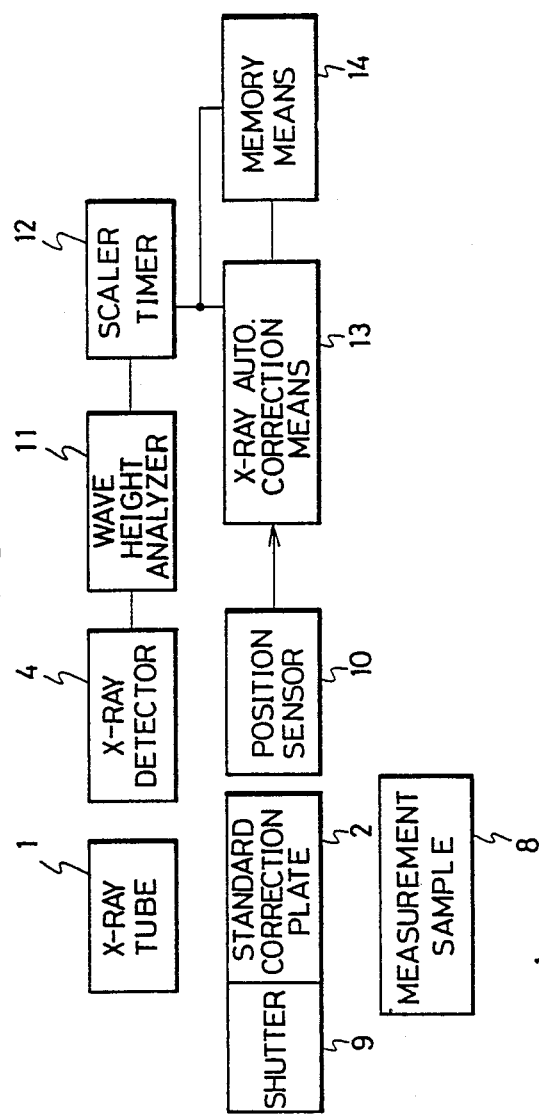
FIG. 3 is a block diagram of the X-ray device of FIGS. 1 and 2, and, FIG. 4 is a diagrammatic view of an X-ray device according to the conventional construction.
Figure 4:
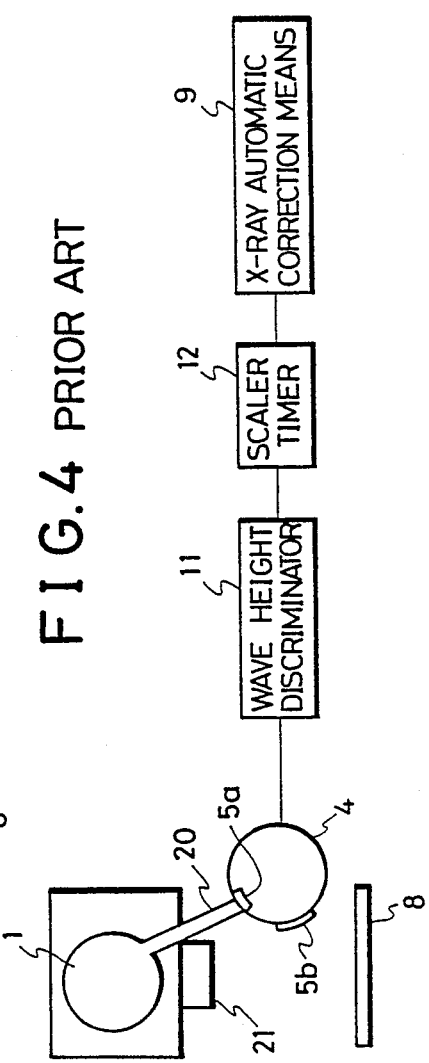
Figure 5:
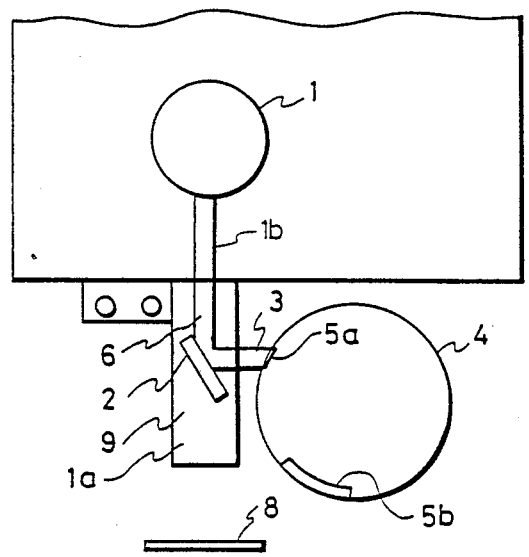
Figure 6:
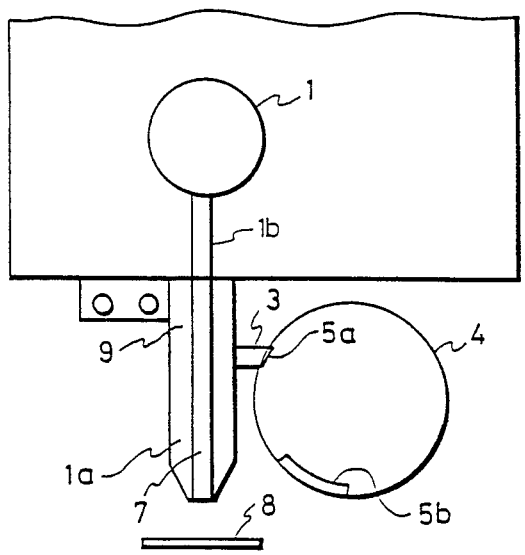

As shown in FIG. 3, the X-ray detector 4 is connected to and passes electrical signals to a wave height analyzer 11. The output of the wave height analyzer 11 is counted by a scaler timer 12 and is passed to an X-ray automatic correction means 13 which is arranged to correct the X-ray tube 1 automatically when there is a variation in the X-rays produced by the X-ray tube 1, e.g. when there is a variation in the wave height and or intensity of the X-rays. The output from the scaler timer 12 is also passed to a memory 14 which is connected to the X-ray automatic correction means 13.

A position sensor 10 is provided which senses the position of the shutter 9 and ensures that the correction in the X-rays produced by the X-ray tube 1 occurs only at a time when the shutter 9 is closed.

The arrangement may, if desired, be such that the fluorescent X-rays which are received by the X-ray detector 4 from the sample material 8 are compared with those which are received from the correcting standard plate 2, the X-ray automatic correction means 13 being required to correct the X-ray tube 1 only when there is a predetermined difference between the two lots of fluorescent X-rays.

Thus in the case of the embodiment of the present invention shown in FIGS. 1 and 2, and X-rays from the X-ray tube 1 are directed onto the correction standard plate 2 by way of the first guide passage 6 only while the shutter 9 is closed. When, however, the correction standard plate 2 is moved together with the shutter 9 to the X-ray open position of the latter, in which the first guide passage 6 is spaced from and out of communication with the passage 1b of the tube 1, then since the third guide passage 7 is positioned over the sample material 8 and since the shutter 9 is moved from the position shown in FIG. 1, X-rays are directed through the passage 1b and third guide passage 7 onto the sample material 8.

Since the position of the shutter 9 is detected by the position sensor 10, the X-ray device is maintained in a correction mode only while the shutter 9 is closed.

Since the corrected X-rays are transmitted to the X-ray detector 4 only during the time that the shutter 9 is closed, the corrected X-rays do not affect the measuring operation on the sample material 8.

In operation, the shutter 9 is first opened so as to direct the X-rays through the passages 1b and 7 onto the sample material 8. The open position of the shutter 9 is sensed by the position sensor 10, and data concerning the intensity and the wave height of the fluorescent X-rays from the sample material is stored in the memory 14. The shutter 9 is then closed and the correction means 13 is so formed that the data concerning the fluorescent X-rays emitted from the sample material 8 which has been so stored in the memory 14 is compared with the data concerning the intensity and the wave height of the fluorescent X-rays from the correction standard plate 2 which has been previously stored in the memory 14. If there is a predetermined difference between the two lots of data, the X-ray automatic correction means 13 effects correction of the X-ray tube 1 to thereby restore the intensity and/or the wave height of the X-rays from the tube 1 to a predetermined value. At the same time, the data concerning the fluorescent X-rays from the sample material 8 are evaluated (by means not shown) so as to indicate the value of a property of the sample material 8 (e.g. the thickness of a surface layer thereon).

During the time that the shutter 9 is closed, the correction standard plate 2 will be irradiated with X-rays from the X-ray tube 1 through the passages 1b and 6 and will itself produce fluorescent X-rays. These fluorescent X-rays from the correction standard plate 2 are directed onto the X-ray detector 4 and their intensity and wave height are evaluated at regular intervals, e.g. intervals of one second, there being means (not shown) such that data relating to the said intensity and wave height are stored in the memory 14 for subsequent comparison with the data relating to the fluorescent X-rays from the sample material 8.

Consequently, the measurement of the sample material 8 does not need to be delayed, as has previously been the case, until a sufficient length of time has elapsed to establish the average value of the intensity and wave height of the fluorescent X-rays from the correction standard plate 2 and until a separate correction step for correcting the X-ray tube 1 has been carried out. In the case of the present invention, the correction of the X-ray tube 1 can be effected immediately at any time when the sample material 8 is not being measured so that the measurement of the sample material 8 is not held up even though the time required for effecting a correction of the X-ray tube 1 amounts to the total time required to obtain data concerning the fluorescent X-rays produced by the correction standard plate 2 and by the sample material 8.

If, for example, the time for which it is necessary to measure the fluorescent X-rays emitted from the correction standard plate 2 in order to obtain a correct measurement is T-seconds, this measurement can be effected by taking the instantaneous measurement of the fluorescent X-rays emitted from the correction standard plate 2 every second, storing these measurements in the memory 14, and obtaining an average value of these measurements during the T-seconds. For example, means (not shown) may be provided for obtaining a running average value of these measurement, which average value is continuously being corrected and which is not cleared from the memory 14 when the data relating to the fluorescent X-rays from the sample material 8 is cleared therefrom.

What is claimed is:

1. An X-ray device comprising: an X-ray tube for generating X-rays; a collimator for collimating the X-rays from said X-ray tube and directing the X-rays to a sample to thereby cause the sample to emit fluorescent X-rays; a movable shutter having said collimator attached thereto for movement therewith and disposed between said X-ray tube 1 and the sample for movement between an open position for permitting the X-rays to be directed to the sample and a closed position for preventing the X-rays from being directed to the sample; an X-ray detector for detecting the fluorescent X-rays emitted from the sample when said shutter is in the open position; a correction standard plate movable with the shutter for receiving X-rays from said X-ray tube and for emitting and directing fluorescent X-rays onto said X-ray detector only when said shutter is in the closed position; and correction means connected to said X-ray detector for automatically correcting for irregularities of the X-ray intensity and wave height when said shutter is in the closed position.

2. An X-ray device as claimed in claim 1; in which said collimator has a first guide hole for guiding X-rays from said X-ray tube to said correction standard plate, and a second guide hole for guiding fluorescent X-rays from said correction standard plate to said X-ray detector when said shutter is in the closed position.

3. An X-ray device as claimed in claim 1; in which said X-ray detector has two opened portions, one positioned for receiving fluorescent X-rays from the sample and the other positioned for receiving fluorescent X-rays from the correction standard plate.

4. An X-ray device as claimed in claim 1; in which the correction means is controlled by a position sensor which sense the position of the shutter.

5. An X-ray device as claimed in claim 1; in which said correction means includes a memory.

6. An X-ray device as claimed in claim 5; in which said correction means includes means for comparing first data which relate to the fluorescent X-rays emitted by the sample with second data stored in said memory and which relate to fluorescent X-rays emitted by the correction standard plate.

7. An X-ray device as claimed in claim 6; including means for periodically storing the second data in said memory at predetermined intervals.

8. An X-ray device as claimed in claim 7; including means for averaging the second data stored in said memory at said predetermined intervals.

9. An X-ray device comprising: means for generating X-rays and directing the X-rays along an X-ray path; a correction standard plate operative when irradiated with X-rays to emit fluorescent X-rays; a movable shutter having the correction standard plate mounted thereon for movement therewith, the shutter being movably disposed in the X-ray path for movement between first and second positions and having a first collimator passage alignable with the X-ray path when the shutter is in the first position for directing the X-rays onto a sample to cause the sample to emit fluorescent X-rays and a second collimator passage alignable with the X-ray path when the shutter is in the second position for directing the X-rays onto the correction standard plate while preventing the X-rays from irradiating the sample; detecting means for detecting the fluorescent X-rays emitted by the sample when the shutter is in the first position and for detecting the fluorescent X-rays emitted by the correction standard plate when the shutter is in the second position; and correcting means connected to the detecting means and operative when the shutter is in the second position for correcting for irregularities of the X-ray intensity and wave height.

10. An X-ray device according to claim 9; wherein the shutter has a third collimator passage for directing the fluorescent X-rays emitted by the standard correction plate to the detecting means when the shutter is in the second position.

11. An X-ray device according to claim 10; wherein the third collimator passage extends transversely to the second collimator passage.

12. An X-ray device according to claim 9; wherein the detecting means has two X-ray receiving openings, one opening being positioned to receive fluorescent X-rays emitted by the sample and the other opening being positioned to receive fluorescent X-rays emitted by the standard correction plate.

13. An X-ray device according to claim 9; wherein the correcting means comprises memory means for storing first data representative of a property of the fluorescent X-rays emitted by the standard correction plate, and means for comparing second data representative of a property of the fluorescent X-rays emitted by the sample with the first data stored in the memory means.

14. An X-ray device according to claim 13; including means for periodically storing the first data in the memory means at predetermined intervals.

15. An X-ray device according to claim 14; including means for averaging the first data stored in the memory means at said predetermined intervals.

* * * * *